(12) United States Patent
Daffer et al.

(10) Patent No.: US 7,503,926 B2
(45) Date of Patent: Mar. 17, 2009

(54) COMBINED SAUNA AND ENVIRONMENTAL CAPSULE

(75) Inventors: Steven J. Daffer, Edina, MN (US); James M. Garrison, St. Louis Park, MN (US); Tarmo Koss, Juri (EE); Lars Sumberg, Tallinn (EE); Tarvo Aulik, Saaremaa (EE); Toomas Kelder, Harjumaa (EE)

(73) Assignee: Visibelle Derma Institute, Inc., Bloomington, MN (US)

( * ) Notice: Subject to any disclaimer, the term of this patent is extended or adjusted under 35 U.S.C. 154(b) by 923 days.

(21) Appl. No.: 10/839,576

(22) Filed: May 5, 2004

(65) Prior Publication Data

US 2004/0260364 A1    Dec. 23, 2004

Related U.S. Application Data

(60) Provisional application No. 60/469,281, filed on May 9, 2003.

(51) Int. Cl.
*A61H 21/00* (2006.01)
(52) U.S. Cl. .......................................... 607/81; 607/82
(58) Field of Classification Search ............. 607/80–91, 607/93, 96, 104, 108
See application file for complete search history.

(56) References Cited

U.S. PATENT DOCUMENTS

| 1,221,163 | A |   | 4/1917 | Frink |
|---|---|---|---|---|
| 1,531,833 | A | * | 3/1925 | Bauer ............................ 4/525 |
| 1,643,528 | A |   | 9/1927 | Thurston |
| 1,797,916 | A |   | 3/1931 | Kruse |
| 2,012,221 | A |   | 8/1935 | Clark et al. |

(Continued)

FOREIGN PATENT DOCUMENTS

DE            725804          3/1944

(Continued)

OTHER PUBLICATIONS

Notification Concerning Transmittal of International Preliminary Report on Patentability.

(Continued)

*Primary Examiner*—Ahmed M Farah
(74) *Attorney, Agent, or Firm*—Westman, Champlin & Kelly, P.A.

(57) ABSTRACT

A personal therapy or sauna compartment is formed with a base, that has a support bed on the interior of the base in which a person can lie. A cover is provided over the base and covers the body of a person lying in the bed, with the head of the person outside of the cover. The bed is supported above massage shower heads that provide massage water impingement upwardly against the back of the person on the bed. Infrared heaters are placed in the cover, and shower heads in the cover provide for comfort and showering the person lying on the bed. A mist head is provided for adding in liquid forms of vitamins, hormones, and other therapeutic elements capable of being absorbed by the skin. The cover has large translucent side panels for the majority of the sides of the panels, and is supported on a central spine frame pivoted at a foot end to the base, with a hoop at its open or head end. The cover hinges to open and close relative to the base.

23 Claims, 10 Drawing Sheets

U.S. PATENT DOCUMENTS

| | | | |
|---|---|---|---|
| 2,096,128 A | 10/1937 | Mortrude, Jr. | |
| 2,240,819 A | 5/1941 | Waly | |
| 2,300,455 A | 11/1942 | Lukats | |
| 2,567,614 A | 9/1951 | Merriam | 128/366 |
| D189,951 S | 3/1961 | Cosper | D83/1 |
| 3,409,915 A | 11/1968 | Jauvais | 4/163 |
| 3,556,088 A | 1/1971 | Leonardini | 128/33 |
| 3,772,713 A | 11/1973 | Roullier | 4/164 |
| 3,945,058 A | 3/1976 | Gardner | 4/163 |
| 4,031,573 A | 6/1977 | Romanoff | 4/164 |
| 4,055,863 A | 11/1977 | Duval | 4/173 R |
| D249,894 S | 10/1978 | Brancaccio et al. | D24/37 |
| 4,130,120 A | 12/1978 | Kohler, Jr. | 128/373 |
| D255,491 S | 6/1980 | Brancaccio et al. | D24/37 |
| 4,258,706 A | 3/1981 | Shank | 128/33 |
| 4,277,855 A | 7/1981 | Poss | 4/524 |
| D275,605 S | 9/1984 | Taylor | D24/38 |
| 4,565,188 A | 1/1986 | Hardie | 128/24.2 |
| 4,671,284 A * | 6/1987 | Wilson et al. | 607/81 |
| 4,712,538 A * | 12/1987 | Hardie et al. | 601/16 |
| 4,833,739 A | 5/1989 | Sakakibara et al. | 4/524 |
| 4,862,526 A | 9/1989 | Berger | 4/53.6 |
| 4,884,574 A | 12/1989 | Hardie et al. | 128/373 |
| 5,047,006 A | 9/1991 | Brandston et al. | 600/21 |
| 5,101,809 A * | 4/1992 | Daffer et al. | 601/52 |
| 5,137,018 A | 8/1992 | Chuprikov et al. | 128/395 |
| 5,228,150 A | 7/1993 | Parker | 4/568 |
| 5,255,399 A | 10/1993 | Park | 4/525 |
| 5,259,380 A | 11/1993 | Mendes et al. | 607/115 |
| 5,292,345 A | 3/1994 | Gerardo | 607/88 |
| 5,304,207 A | 4/1994 | Stromer | 607/3 |
| 5,416,931 A | 5/1995 | Wolfenden et al. | 4/524 |
| D360,469 S | 7/1995 | Panelli et al. | D24/202 |
| 5,441,529 A * | 8/1995 | Dorsch | 607/82 |
| 5,447,527 A | 9/1995 | Waldman | 607/88 |
| 5,511,254 A | 4/1996 | O'Brien | 4/532 |
| 5,546,678 A | 8/1996 | Dhaemers | 34/275 |
| 5,645,578 A * | 7/1997 | Daffer et al. | 607/91 |
| 5,891,186 A * | 4/1999 | Daffer et al. | 607/91 |
| 6,004,344 A * | 12/1999 | Fujii | 607/91 |
| 6,497,717 B1 * | 12/2002 | Daffer et al. | 607/83 |
| 6,623,511 B1 * | 9/2003 | Daffer et al. | 607/82 |

FOREIGN PATENT DOCUMENTS

| | | |
|---|---|---|
| DE | 39 15 008 A1 | 11/1990 |
| DE | 197 37 859 A | 3/1999 |
| EP | 0 986 985 A1 | 3/2000 |
| FR | 1 005 211 | 4/1952 |
| FR | 2 086 905 | 12/1971 |
| FR | 2 629 343 | 10/1989 |
| FR | 2 803 512 | 7/2001 |
| GB | 1 490 381 | 11/1977 |
| JP | 8 112302 | 5/1996 |
| JP | 11114008 | 4/1999 |
| JP | 2000350767 | 12/2000 |
| WO | WO 00/02491 | 1/2000 |
| WO | WO 00/61060 | 10/2000 |
| WO | WO 01/49238 A | 7/2001 |
| WO | WO 03/034971 | 5/2003 |

OTHER PUBLICATIONS

International Search Report relative to PCT/US2004/014112.
Written Opinion relative to PCT/US2004/014112.

* cited by examiner

COMBINED SAUNA AND ENVIRONMENTAL CAPSULE

The present application is based on and claims the benefit of U.S. provisional patent application Ser. No. 60/469,281, filed May 9, 2003, the content of which is hereby incorporated by reference in its entirety.

BACKGROUND OF THE INVENTION

The present invention relates to a combination personalized compartment forming a sauna and environmental capsule for a person to receive various therapeutic environmental conditions for relaxation and/or therapy.

In the prior art, various environmental capsules have been advanced, including, for example, the structure shown in U.S. Pat. Nos. 5,101,809 and 6,497,717.

SUMMARY OF THE INVENTION

The present invention relates to a self-contained, personal therapy unit, and comprises a personal compartment including sources of heat, shower, air control, light, steam, and misting spray for herbal and vitamin therapy. The personal compartment is made with a base supporting a bed, with a cover that has a frame to permit obstructed sides, covered with a translucent, pebble surface plastic material so that the interior lights will provide a glow along the translucent plastic surfaces, the covering of the open sides is a unitary molded shell for integrity and enhanced appearance. Various therapies for the person supported on an internal bed are provided.

A known vibrator for the bed is provided. Massaging water spray or shower heads are below the bed for providing a hydro-massage action along the spine and lower back of a user, for relaxation massage therapy. Foot massage hydro heads are also provided under the feet of a person lying on the bed.

Shower heads (Vichy shower) are also provided overhead in the cover, above the person lying on the bed.

Infrared heaters are provided in the cover to direct heat down onto the person lying on the bed. Showering is blocked when the heaters are operating. The bed can be vibrated as has been done in previous saunas, at the same time as the shower or heat is used. The heaters and showers cannot be used at the same time.

The cover is hinged to the base at the foot end and extends up to the shoulder area of the user. The user's head is supported on a head pillow on the upper side of the base of the compartment to the exterior of the cover. An overhead pivoting panel at the head end of the cover carries the controls and a function display screen. The pivoting panel can be moved from a generally horizontal position where it can be observed and is accessible to the person lying on the bed, to an upright position where it is observable and can be controlled by an attendant for various treatments under the control of the attendant or operator.

The shower heads can be connected for individual control through suitable solenoid valves, operated from the control panel, and software is provided so either a personally selected or a programmed regime can be undertaken. The control can be under the supervision of a therapist.

The cover is constructed in a unique manner with a central overhead frame or spine, made of spaced aluminum tubes, and forming a channel receptacle in which water and control lines and shower heads can be installed. A cover is placed over the spaced aluminum tubes to cover the chamber. The aluminum frame or spine supports a yoke or hoop frame member at the head end of the cover, about in line with the shoulders of a person lying on the bed. A main cover support frame is provided at the foot area for hinging the cover spine frame to a base frame. The base has a tripod foot support with a pair of legs at the foot end that are spaced apart, and a relatively large footprint single pedestal under the head end of the base. This provides a stable support, without rocking, and thus does not cause a sense of insecurity.

Receptacles are provided for aromatherapy materials, and also for solutions of vitamins and other materials, that can be misted onto the user. Essential oils and the like can be provided. A steam generator and steam outlets are provided for use, as well.

The valves and controls are all located in a compartment at the foot end frame and are easily accessible and plumbed. Light sources are provided on the base at the foot end directed rearwardly toward the head end. The lights are made to provide six colors controllable by the user for chromatherapy. The translucent cover side panels provide a glow on the interior and the glow is visible at the exterior. The colors are selected to provide a soothing or a healing effect.

DETAILED DESCRIPTION OF THE ILLUSTRATIVE EMBODIMENTS

Figure 9:
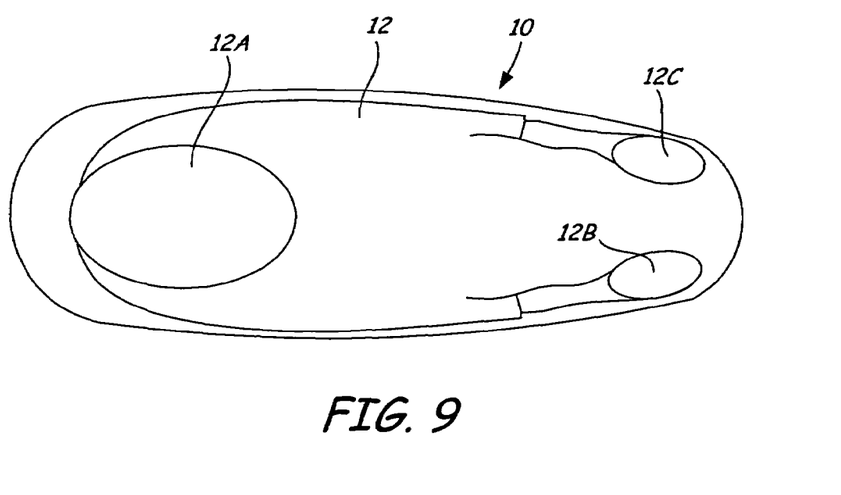
FIG. 9 is a bottom plan view of the base and compartment.

A therapy compartment indicated generally at 10 includes a base unit 12, and a cover 14 hinged together about a hinge axis 16 at a foot end 17 of the compartment 10. The base 12 is supported on a three-point leg system, including a large footprint pedestal 12A with a single area of contact shown at 12A, and a pair of forward legs 12B and 12C (See FIG. 9) so that there is a tripod-type support for the base. The legs 12A and 12B at the foot end provide stability, in combination with the pedestal 12A without any rocking or problems with unevenness of a support floor.

Figure 6:
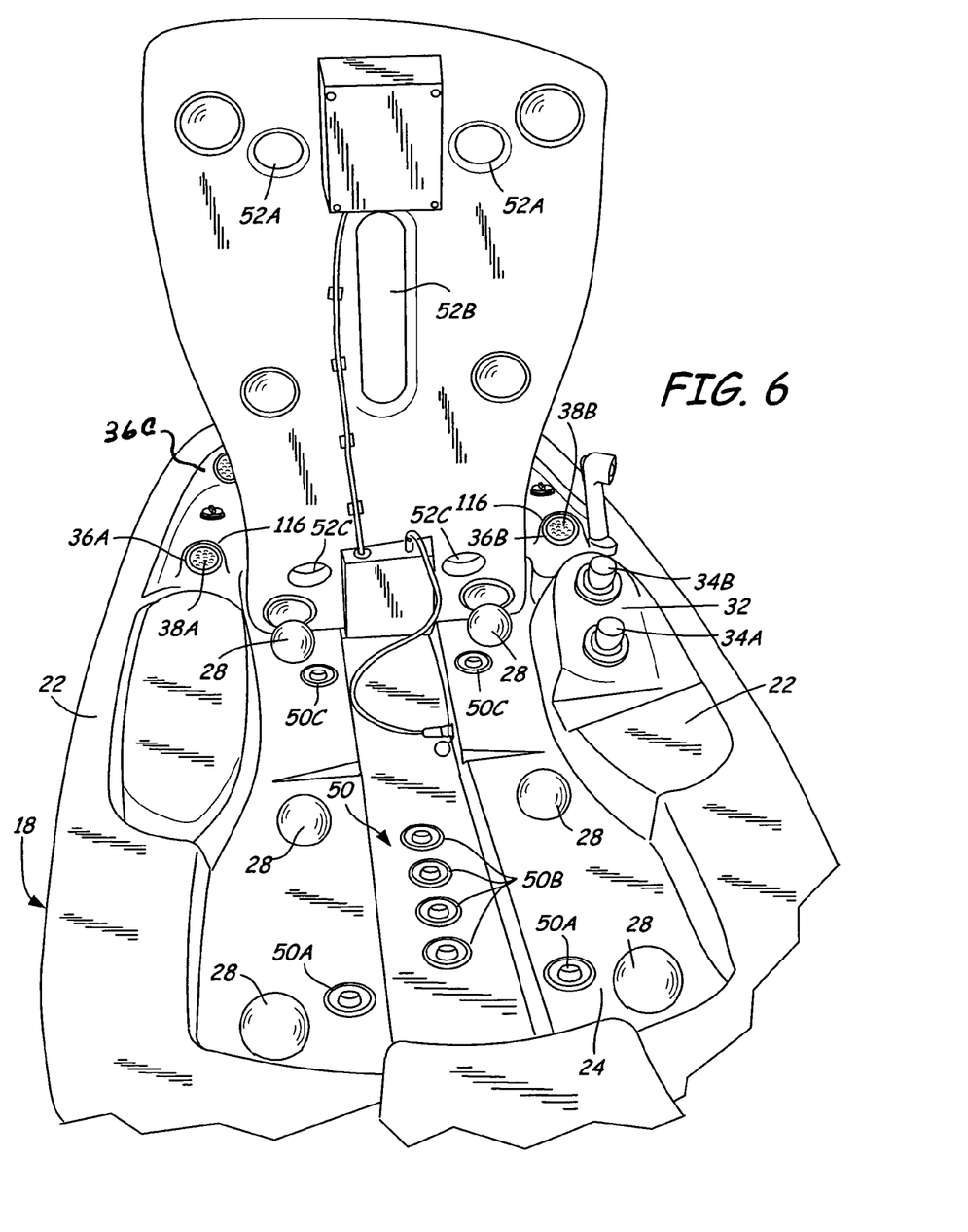
FIG. 6 is a detailed view of the support bed with the support pad lifted showing the shower heads that are provided under the bed.
Figure 7:
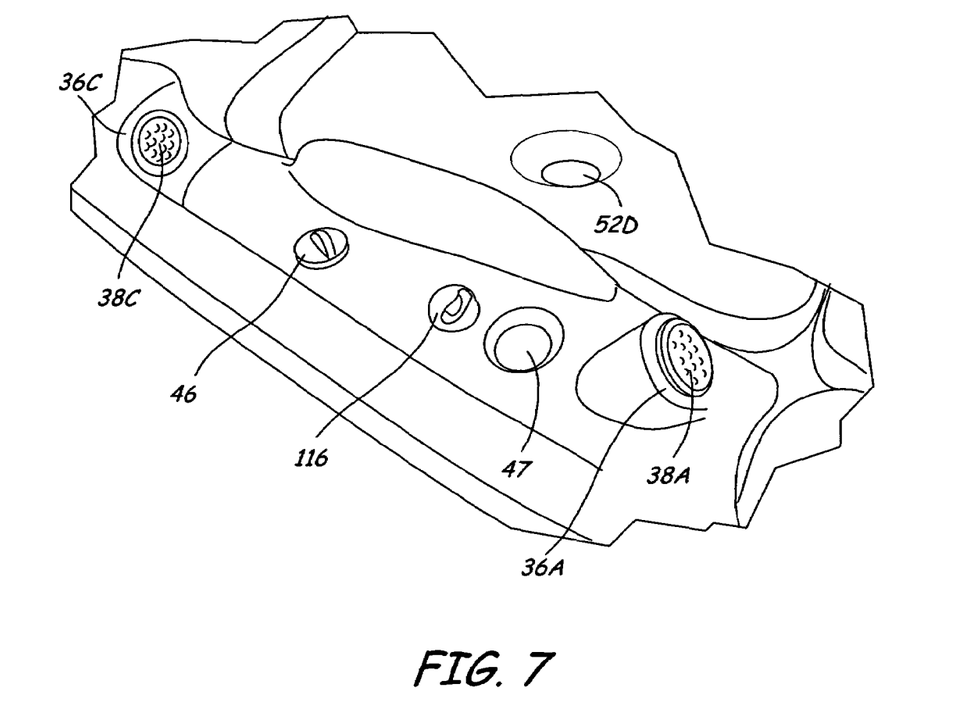
FIG. 7 is a fragmentary side perspective view showing details of features adjacent the foot end.

The base 12 includes a bed platform 18, that is supported on the interior of the base with suitable members 19, that are shown schematically as part of the base frame 70. A chamber 30 is formed beneath the platform bed 18. The bed platform is molded from plastic or fiberglass to be integral with or supported on the molded base 12. The outer molded shell portions of the base are supported on frame 70. The bed support 18, as can be seen in FIG. 6, is molded with a rim member 22 that is raised to form a recess or trough 24 in the center portions of the bed. The recess 24 is molded so that water will drain into the recess and then down to a drain opening into a waste receptacle of drain line of suitable design.

Various components can be housed in the chamber 30 of the base or pedestal below the bed. The rim 22 can be formed to slope inwardly for drainage, along the sides of the recess 24.

The recess 24 is covered with a support mattress or pad 26, that can lift up, as shown in FIG. 6. The mattress or pad is supported on resilient ball supports 28 of conventional design so that when a vibrator (not shown) is used and operated, the ball supports provide for a resilient mounting of the mattress or pad on which a person lies. Vibrators can be controlled as to intensity (amplitude) and frequency as taught in the prior art.

The molded bed support 18 also includes sloped or incline panels 32 on the rim 22 facing toward the head end, on which the shower water main control valves 34A and 34B can be mounted. Also, light support panels 36A, 36B, 36C, and 36D are formed on the rim and inclined upwardly and generally face toward the head end. Each of these light supports 36A-36D include multi-colored LED lights 38A-38D, that will provide for a light projection rearwardly toward the head of the user that is lying on the pad or mattress 26. The lights thus can be directly viewed and they will provide reflected light.

Figure 3:
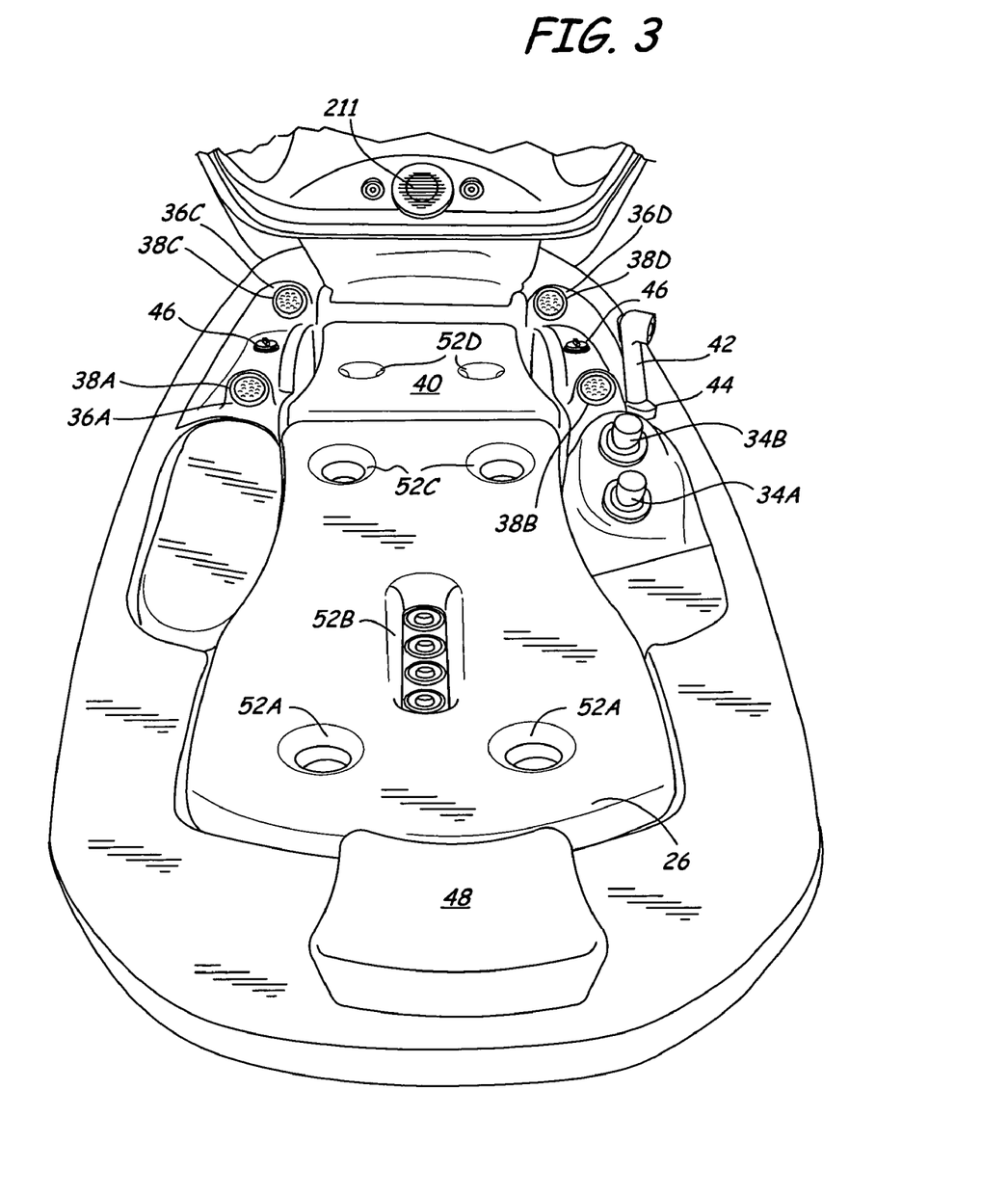
FIG. 3 is a view from the head end of the compartment with the cover open, showing the arrangement of the support bed.

It should also be noted that the bed or mattress 26 is covered with a waterproof cover, because of the shower and hydro massage therapy that is provided. The bed or mattress is a cushion that supports the user adequately. Additionally, as can be seen in FIG. 3, the foot portion has a separate cushion 40, that supports the feet and can be individually removed. It also is formed to provide for drainage.

As shown in FIG. 3, a hand-held shower head 42 is provided and is removably supported in a fitting 44 in the rim 22. The shower head can be pulled out for hand-showering, using suitable controls, as well as being used for rinsing the compartment. Cups 47 for containing aromatherapy material are provided and supported in molded in receptacles.

A pillow 48 is provided at the head end, and as will be explained, this will be outside of the cover 14.

Thus, the base 12 can be a molded unit with an interior framework of suitable design to provide the space 30 for the various components, such as water tanks, pumps, drain conduits, and piping for various shower units.

As shown in FIG. 6, the bed panel recess 24 has a base wall 24A that mounts a plurality of massaging shower head shown generally at 50. These include a pair of massaging shower heads 50A, which are underneath the shoulder area of a person lying on the bed, and a series of massaging shower heads 50B that are aligned with the spine of a person lying on the pad or mattress. As shown, there are four of the massaging shower heads 50B in the mid-portion and lower portion of the back of a user lying on the bed. The massaging shower heads 50A and 50B project sprays of water of desired and variable intensity up against the shoulders and back of the user for hydro massaging, and relaxation therapy. As can be seen in FIG. 3, there are openings 52A and 52B in the pad or mattress 26 above these shower heads. In FIG. 3, it can be seen that openings 52A and 52B permit massaging water to move against the body of a person lying on the bed.

Additionally, there are a pair of leg massage shower heads 50C under the leg area of a person lying on the pad or mattress 26, and in the chamber 24. Openings 52C as seen in FIG. 3 can be provided above the massage shower heads 50C.

In FIG. 3, additional foot massage shower head openings 52D are shown, and the shower heads 50D are provided under these openings 52D. There are thus massaging shower heads under the areas of the body where muscles can benefit from steady or pulsing hydro massages.

Figure 2:
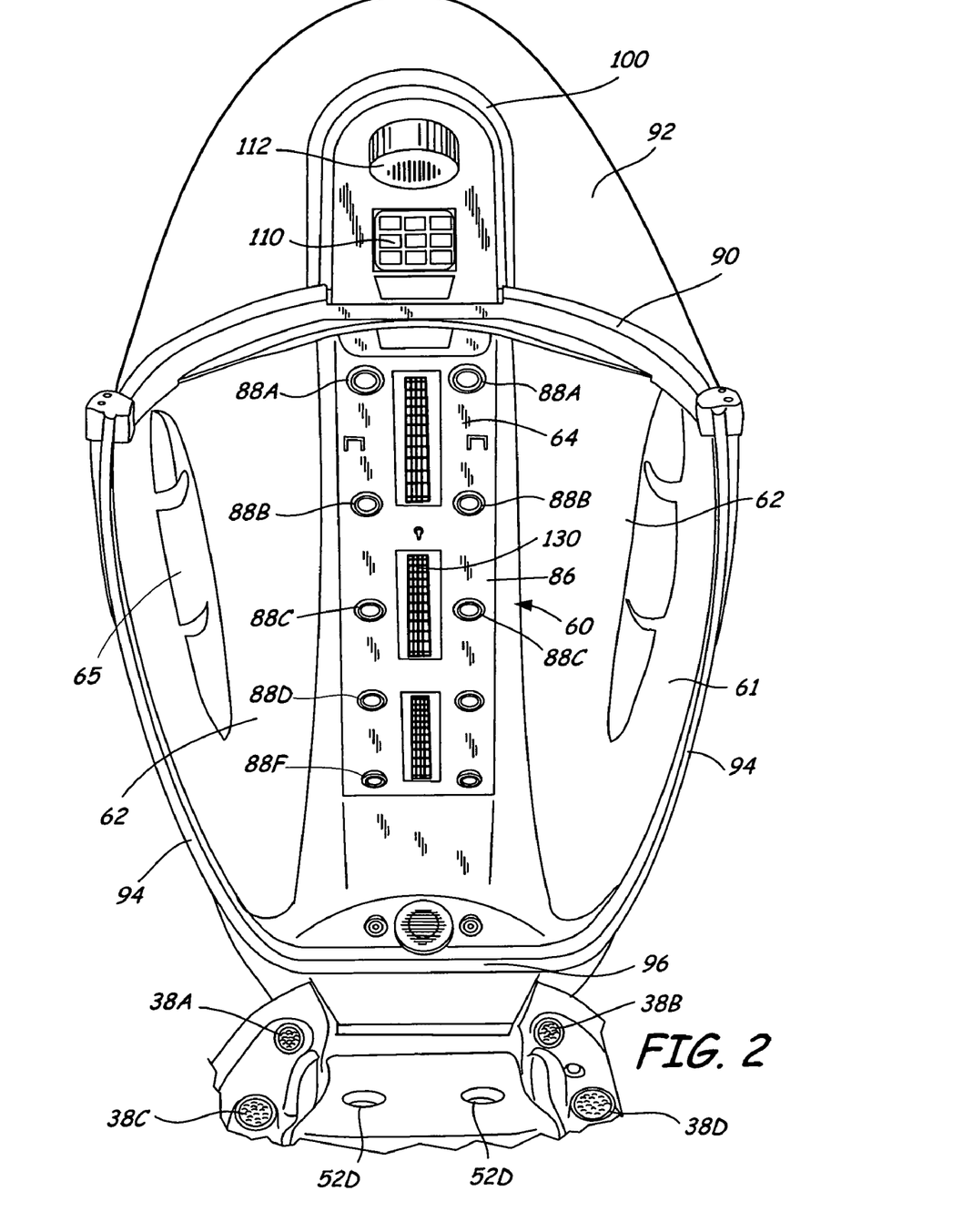
FIG. 2 is an end view of the cover in an open position and a fragmentary portion of the base looking from the head end toward the foot end of the compartment.

Cover 14 is constructed in a unique manner, with wide side openings that will permit natural light to the interior and a "glowing" of the colors projected by the lights 38A-38D. The cover 14, as can be seen in FIG. 2 in its open position, is hinged at the base end as previously explained, and has a center spine frame 60, and has a translucent or semi-transparent unitary panel 61 that has a pair of side panels 62. The single unitary molded plastic member 61 includes the panels 62 and a center portion 64 that underlines the spine or center frame support members 60. The side panels 62 have exteriorly facing recesses 65 for handles 67 for lifting the cover.

Figure 5:
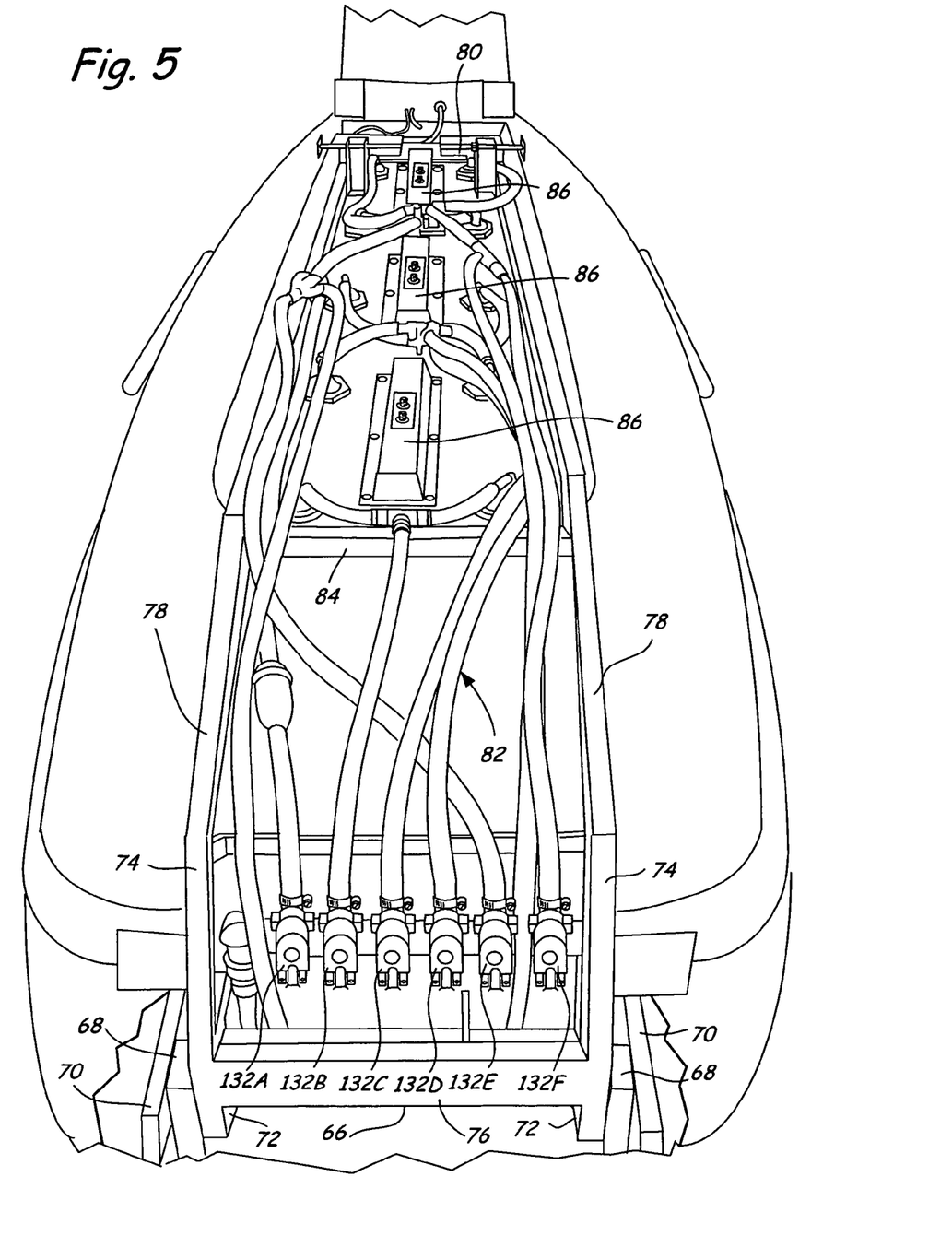
FIG. 5 is a view from the foot end of the bed showing the spine framework, and the chamber for carrying the various lines and controls.

As can be seen in FIG. 5, for example, the spine or center frame support member 60 is supported on a strong aluminum tubing frame 66 at the foot end of the base. The frame 66 is hinged or pivoted to a base frame 70. (See FIG. 5). A pair of support arms 68 are attached to the frame 70 of the base, and a pair of arms 72 are attached to the frame 66. These arms 68 and 72 are pivoted together with suitable bolts.

The frame 66 has uprights 74 on opposite sides thereof that are joined together with a cross piece 76, and then spaced apart longitudinally extending tubes forming side member tubes 78 extend over the top of the bed to form side members for the spine or center frame 60. The side members 78 are spaced sufficiently far above the mattress or pad 26 to provide the necessary space for the person lying on the bed. The frame side members 78 taper together toward the head end, are held with one or more cross members 80, including one at the head end. The center portion 64 of the molded plastic translucent cover liner panel 61 is recessed to go underneath the side members 78. This spacing and the bottom formed by center panel 64 provide a chamber region for holding various water lines and control lines indicated generally at 82.

Cross members 84 can be provided to support infrared heaters 86 that are spaced along the length of the bed to overlie the body of a person lying on the bed. The cover 14 also supports the Vichy shower heads along opposite sides of the center line of the cover, as can be seen in FIG. 2, and these shower heads 88 are made so that they can be controlled in pairs, or in other words, the showers 88E, for example, that are laterally aligned, can be plumbed together, and the four shower heads 88A and 88B can be operated as a unit or individually. Shower heads 88C and 88D also can be operated together or in pairs. If desired, the heads can be individually controlled or all controlled together, as well.

The infrared heaters 86 can be also individually controlled and can be controlled as to the amount of power being provided so that the heat generated is controlled.

The shower heads 88A-88E are mounted on suitable supports on the frame spine or center, and open through openings in the plastic molded member 61 in the center portion 64. The openings in the molded member 61 can be sealed around the shower heads.

The side frame tubes 78, and cross members form the spine frame 60, and at the head end, the side frame tubes are joined with a collar or hoop member 90 that is also made of tubing. The hoop member 90 is open at the bottom and provides structural support at the head end of the cover. A shield portion 92 can be provided on the exterior of the hoop or part circular head end frame.

Longitudinal cover edge frame members 94 are then joined to the lower end of the hoop 90, and extend longitudinally toward the foot end where they are joined with a cross member 96 that is attached to the frame 66. The frame members 94 support the lower edges of the side panels 62 of the cover member.

Thus, the spine frame 60 and the other support members for the cover are made of lightweight but strong aluminum tubing. The cover is made with a longitudinal extending spine or center frame 60, a foot end frame 66, and a head hoop frame, along with longitudinally extending edge members for supporting and carrying the molded plastic cover 61 that is translucent and is provided with a pebble finish to enhance the color diffusion when the lights are on.

Figure 4:
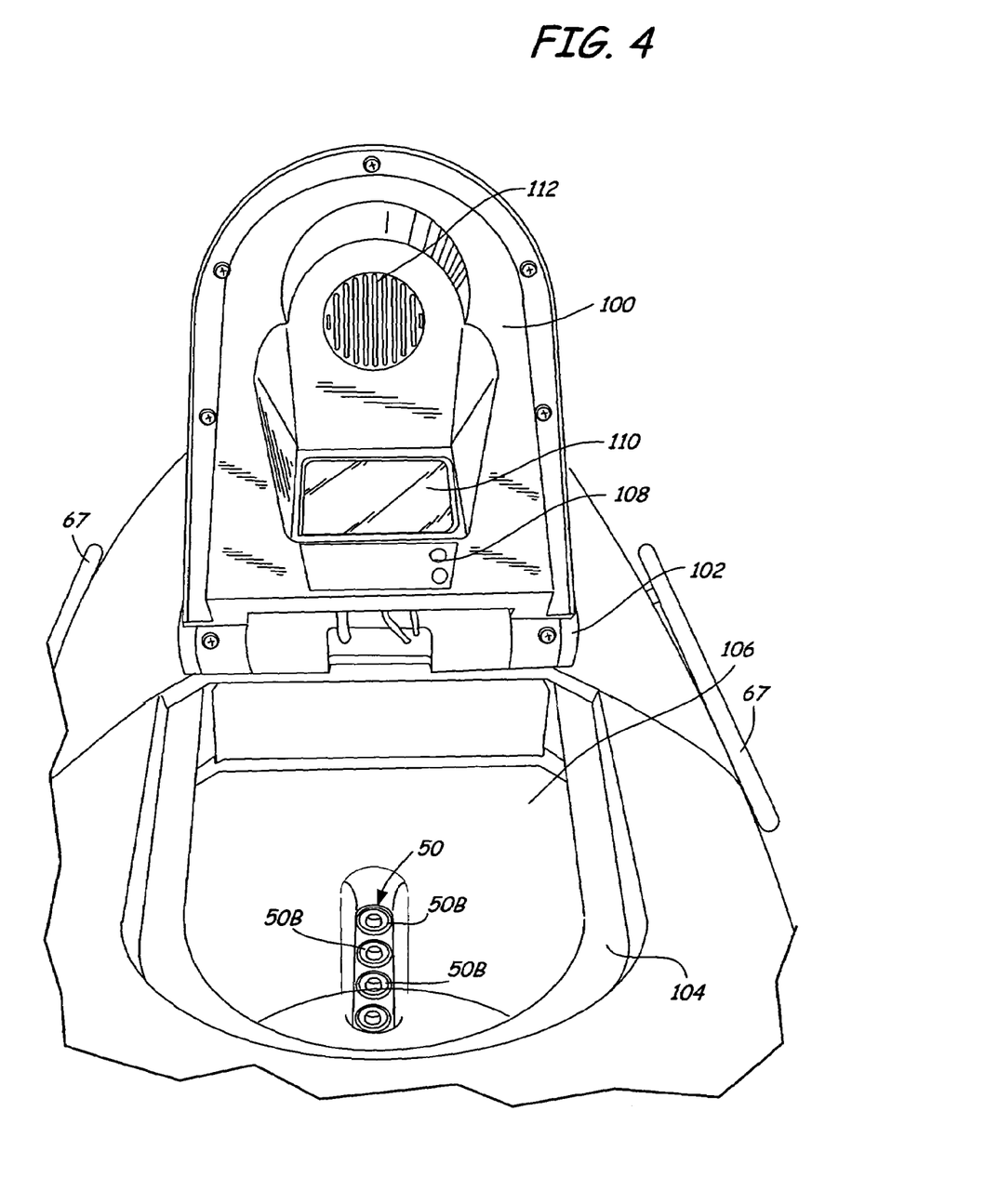
FIG. 4 is a view from the head end with the control panel member in a raised position for use by an operator.
Figure 8:
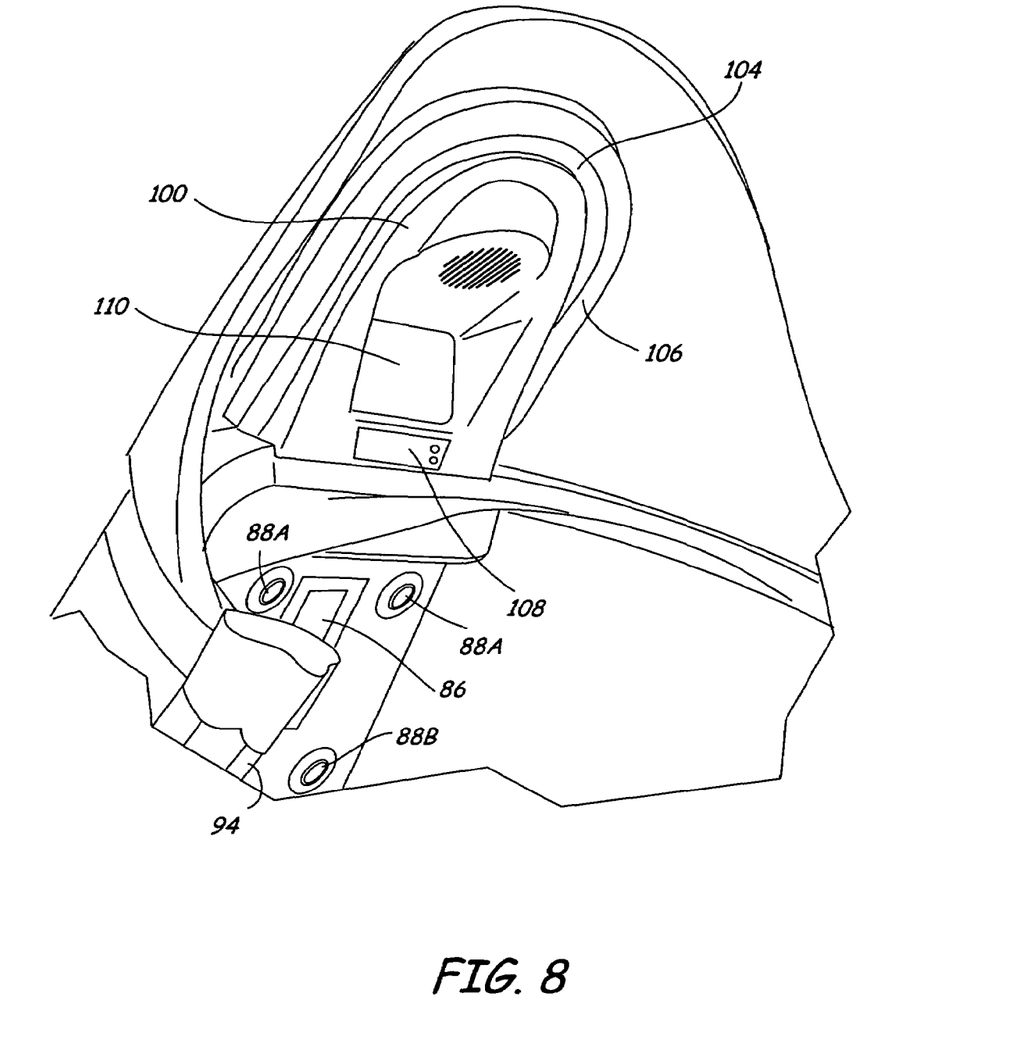
FIG. 8 is a perspective view at the head end of the cover looking upwardly to show the control panel in its position usable by a person lying on the bed, and showing the framework assembly.

Another feature of the present invention is a control panel housing 100 that is hingedly attached about a transverse hinge 102 to the head end of the spine member 60 above the hoop frame. The panel housing is movable from a position where it rests on a provided recess 104 around an opening in the shield or extension 92, as shown in FIG. 4. The head extension 92 can be molded integrally with the cover sheet 61, and the recess portion 104 defines an open area 106 through which the control members 108 can be reached by a person lying on the bed, when the control panel housing 100 is in its position shown in FIG. 8. A display screen 110 is provided for indicating the status of various functions or devices controls that are controlled by the controls 108.

Figure 1:
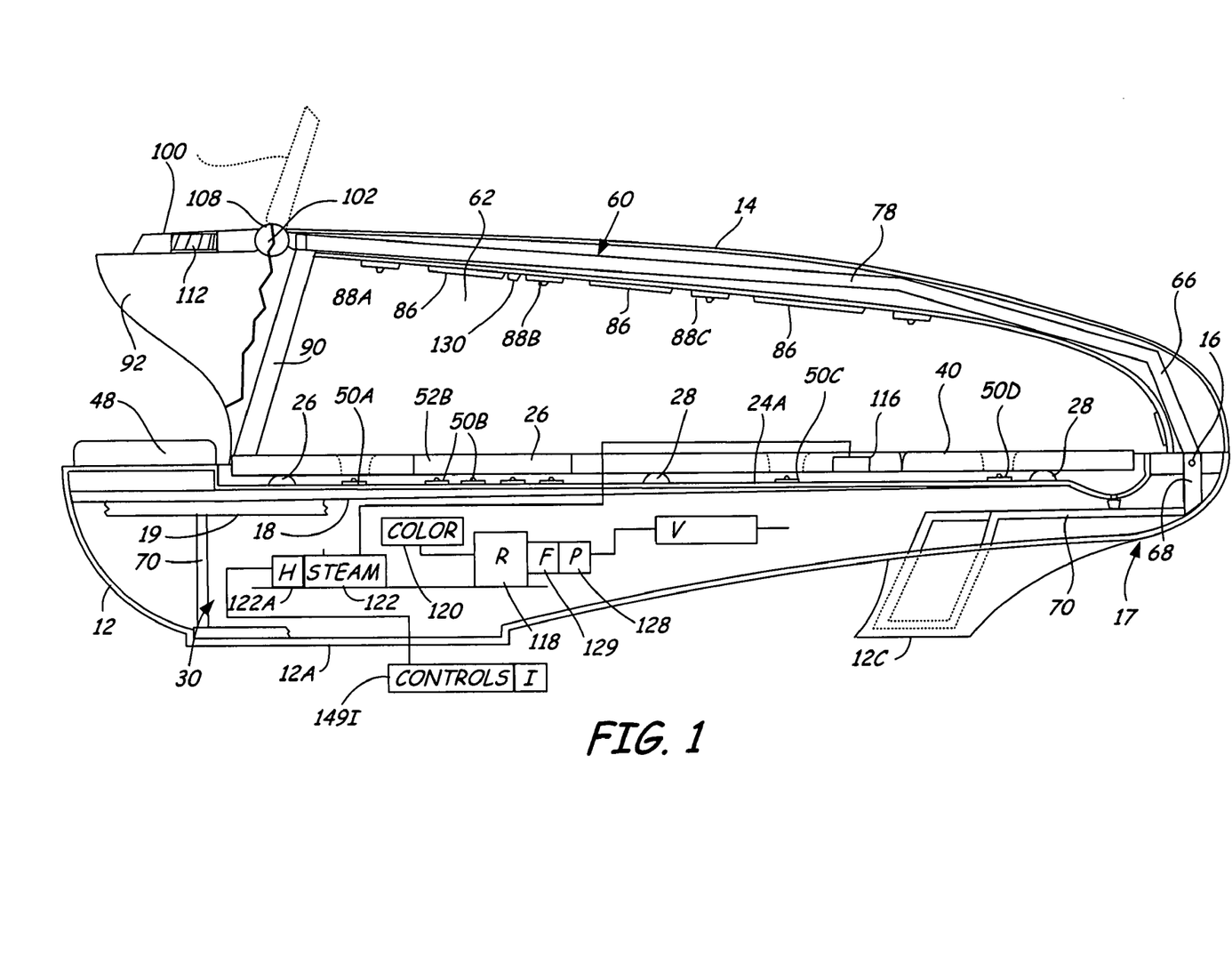
FIG. 1 is a side sectional view of a therapy compartment made according to the present invention.

The control panel housing 100 can be pivoted upwardly about its hinge to the position shown in FIG. 4, and in dotted lines in FIG. 1, where the controls 108 are accessible to an operator standing along side of the compartment. As can be seen, the control area 108 is no longer easily accessible to the person lying on the bed.

A fan and outlet 112 can also be included in the housing 100. The control wiring can pass between the tubular members 78 of the spine frame 60.

The underlying individual massage shower heads 50A, 50B, 50C and 50D are controlled individually as sets, as are the shower heads 88A-88E.

In addition, a steam generator 122 can be provided to supply steam to steam outlets generally shown at 116 shown in FIG. 6, for example. The steam outlets can be swiveled to direct steam in a desired direction.

The chamber 30 below the bed can be used for housing a liquid reservoir 118, and this includes suitable color inputs 120, if desired, as detailed in application Ser. No. 09/706,946, filed Nov. 6, 2000, incorporated herein by reference. A steam generator 122 can be provided, along with a steam generator heater 122A. The steam outlets 116 are shown schematically in FIG. 1 as well.

Reservoir 118 is shown only schematically, but it can be understood that several reservoirs can be used if desired, and a pump provided, as shown at 128, for providing water under pressure to a manifold control. A filter 129 also is provided.

One other aspect that is added in the present invention is a mist head indicated at 130, which is a fine mist that is connected to a source of liquid vitamins or hormones that can be absorbed through the skin. The fine mist head 130 is above the chest area of the person lying on the bed, so that the mist will fall gently down onto the chest and will be absorbed by the skin. This function is also detailed in U.S. patent application Ser. No. 10/379,975, filed Mar. 5, 2003, which is hereby incorporated by reference.

The source of the liquid vitamins and hormones is through containers in the chamber 30, and accessible by filler caps shown in FIG. 3 at 46.

Individual solenoid valves for controlling the shower heads 88A-88E are shown in FIG. 3, for example, and can comprise individual solenoid valves 132A, 132B, 132C, 132D and 132E. These valves can be connected and used as desired, for example, if one valve supplies plain water to four heads, another valve can be used to provide water that is colored, or has additives to the same shower heads. A valve 132F can be used for controlling the flow of liquid vitamins or hormones and other therapeutic materials to the mist head 130 under the controls from the control panel 108.

In FIGS. 10A, 10B, 10C and 10D, typical control arrangements are shown. The water temperature can be controlled with a thermostatic control 146, with the ability to raise and lower the temperatures through controls 146A and 146B, and then on the screen, the indication of the temperature can be made with a digital representation 146C. Sources of shower and massage water also can be controlled as desired, and come from the reservoir 118, or from a hot or cold tap, if desired, along 182 and 184. These lines can be hooked up individually, if desired.

The individual showers can be controlled as previously indicated. The shower heads can be set to spray or provide a mist or a rain. Shower heads that provide such use are conventional. A shower timer 148 can be used with the control system, and the time can be increased or reduced with suitable controls 148A and 148B.

Start and stop switches 149A and 149B can also be provided on the shower control system. These are shown schematically and can start and stop the overhead selectable shower, the back massage and foot massage heads, and the hand-held shower. The on/off controls are tied into an interlock circuit 149I that interlocks with the infrared heaters, so the heaters cannot be used during showering or when steam is on.

Figure 10A:
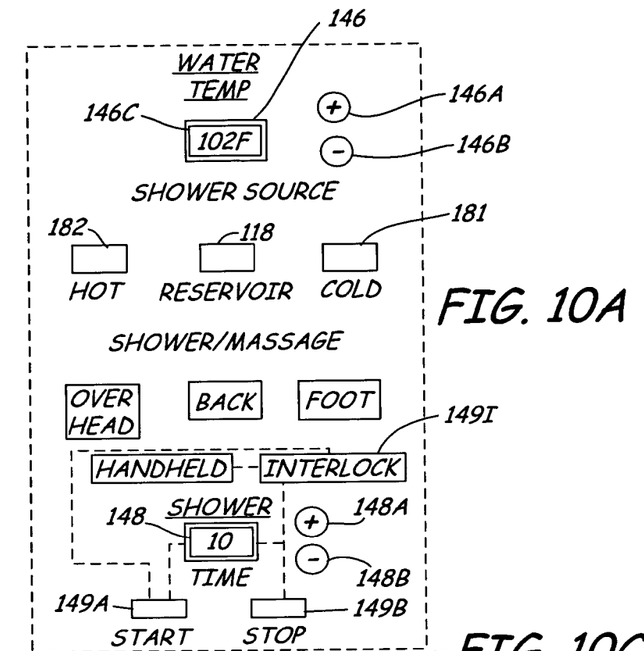
FIGS. 10A, 10B, 10C and 10D are schematic representations of the controls available on the therapy compartment.
Figures 10B, 10C, 10D:
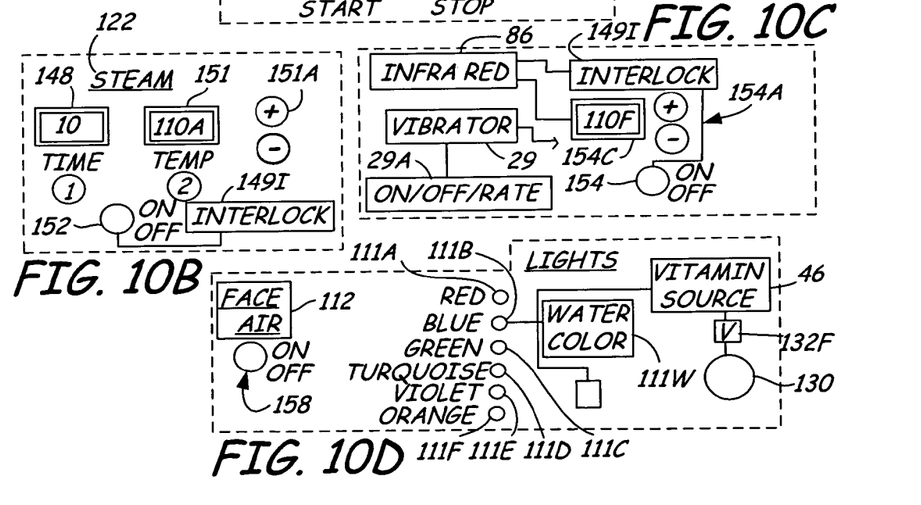

Steam cycles can be controlled as shown in FIG. 10B with a timer 149, and the temperature also can be controlled with a control 151 to either increase with the control 151A or decrease the temperature with the control 151B. The on/off control 152 is on the control panel as well, and operates through interlock circuit 149I.

The infrared heaters 86 have on/off controls 154, as shown in FIG. 10C, with the temperature indicating on the screen as shown at 154C, and the controls can include an intensity control 154A. Again, the interlock circuit prevents operating the showers or massage head at the same time as the infrared heaters are on.

The vibration control for vibrator 29 as shown as control 29A, including on/off, rate (frequency) and intensity.

The air flow from the fan behind air flow outlet 112 can be controlled with a face air on/of switch 158, and the lights can be controlled through a suitable control indicated generally at 111A, 111B, 111C, 111D, 111F and 111G for the different colors.

The lights 38A-38D are LEDs and the different colors are provided either from original light sources or a blend of lights, as desired. The solenoid valve 132F is illustrated for controlling flow from the vitamin source or hormone source 46, which is a liquid that can be misted through the mist head 130. The lights can also be connected through interlock circuit 149I, if desired.

If water color is desired, it also can be controlled and coordinated with the lights as desired from sources 111W.

Figure 11:
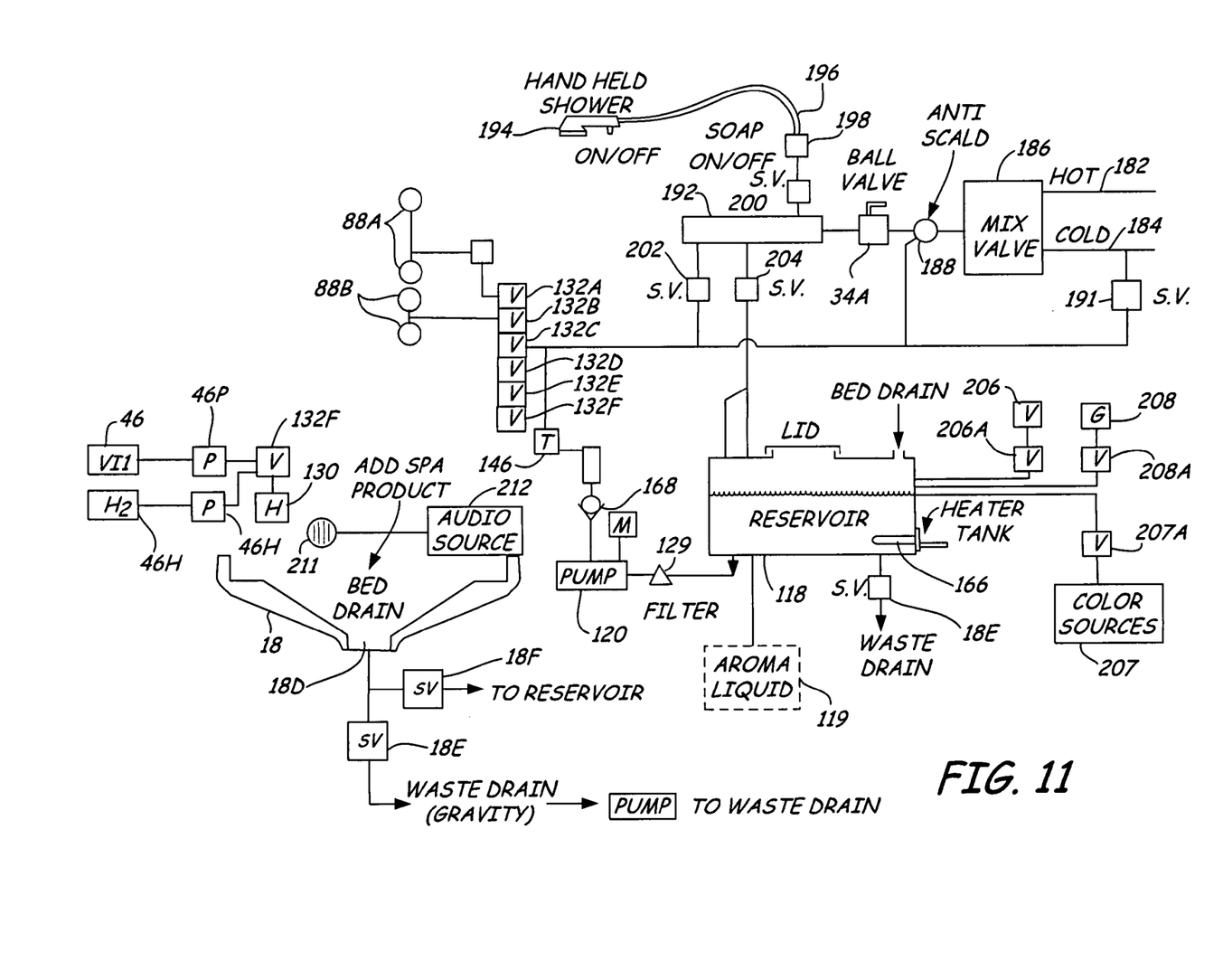
FIG. 11 is a schematic representation of the plumbing and valves used with the present invention.

FIG. 11 provides a schematic diagram of the various valves and the like that can be used. On the left hand side in FIG. 11, the bed 18 is represented, and it can have a drain 18D. A solenoid valve 18E can be used for controlling the drain, and also if desired, a valve 18F can be used for providing the drain water back to the reservoir through a suitable filter or treatment. A solenoid valve 18E can control flow to a pump to a waste drain, if desired. Various spa products can be added as represented schematically, and the excess will all be drained out through the drain 18D.

The source of vitamins is indicated at VS1 and 46, and can be injected through a pump 46P and the valve 132F to the mist head 130 for misting onto a person lying on the bed in the compartment. A hormone source, for example, such as that shown at H2 at 46H, can be controlled through a separate pump 46P-1, and also through the same valve 132F to the mist head 130, or to a separate mist head if desired.

The water reservoir 118 is illustrated, and if desired, aroma liquid can be provided from a source to the reservoir. The reservoir can include a tank heater 166, for controlling the temperature of the water, through the control 146A and B (FIG. 10) as explained.

The pump 128 is connected to a source through a filter 129 takes the liquid from the reservoir and passes it through a check valve 168, and the temperature control 146, to valves 132A-132F. The valves control flow to the individual shower heads that are connected in parallel shown only schematically in FIG. 11. Also, a separate pump can be used for providing flow to the massage heads 50.

By way of an alternate source of water for a shower system, external connections can be provided to the shower lines from outside water sources. Hot and cold water lines 182 and 184 are provided through a valve 191 which can direct flow of cold water to the overhead shower, as shown. If desired, a mix valve 186 can be used for mixing hot and cold water, and an anti-scald valve 188 can be branched into the lines leading to the shower heads. Servo valve 191 is a cold water bypass that can be controlled from the control panel to provide cold water if a cold rinse is desired.

The hand-held shower head shown at 194 can be used with a separate on/off valve, connected with a hose 196 through a soap dispenser or injector 198, if desired, and controlled by a servo valve 200 from a water manifold 192. The water manifold can receive water from the hot and cold tap lines, through one of the valves 34A or 34B, if desired, and then through servo valves 202 and 204 that can be opened or closed to provide flow to or from the hand held shower if desired. These valves also can be controlled through interlock circuit 149I, so they will not be openable if the infrared heaters are on.

Thus, a wide range of shower conditions, vitamin additions and other treatments can be used. The shower heads underneath the body provide for massage effects that are therapeutic and can be enjoyed by the user.

If desired, various color sources 207 can be utilized. These can be coordinated with the colored lights for a shower that is provided with chromatherapy benefits. The color sources 207 can be directed to a reservoir 118, or generally it would be a separate reservoir, that would be provided to the shower system. Yellow color 206 can be controlled through a solenoid valve 206A, and green color, for example, can be controlled from a source 208 through a valve 208A, and each of the individual colors then can be used as a general color source as indicated at 207. These can be mixed into the shower at any desired ratio, and in a suitable location.

The present device provides for control of various operations, including the vibration bed intensity, and frequency, and this can also be pulsating so it would vary in intensity across a known cycle. Face air can be turned off and on as desired, and this is through the fan that is shown. Controls would be touch controls, and the functions would be displayed on the screen. Software is provided for control, as is well known.

There also is an audio system, as has been shown in the prior art therapy capsules, and the audio volume and speaker on/off controls for the speaker and audio source 211 and 212 (see FIG. 2) can be provided. Light brightness, as well as light color selection is available, and air flow onto the face can be at various levels.

The colors provided can be LEDs or any desired color. As shown, red, blue, green, turquoise, violet and orange are provided. The lights can have known fading control, so that after a certain length of time, they can be programmed to fade, as well as being manually controllable.

As was stated, the bed vibration can be selected as to intensity and mode, the steam is selectable on and off, and temperature can also be selected. Aromatherapy is provided, as well as the ability to vary the intensity of the infrared light. The overhead or Vichy showers can have various modes, and the vitamins or hormones from the misting head can be provided at desired times. The back massage and the foot massage can also have various modes for pulsing operation at timed intervals, and the like.

It is pointed out that the interlock control 149I cuts out the misting, and the showers as well as the back and foot massage when infrared heaters are being used.

The interlock control is set so that high infrared heat settings cannot be selected in conjunction with the steam, and as stated, when showers or misting is used, the infrared heaters cannot be turned on.

Several preset programs can be used in a known manner, using software controls that are known.

Although the present invention has been described with reference to preferred embodiments, workers skilled in the art will recognize that changes may be made in form and detail without departing from the spirit and scope of the invention.

What is claimed is:

1. A personal therapy compartment comprising a base unit having a head end, a foot end and spaced side edges, and having a support bed on an interior between the side edges, a cover hingedly connected to the base unit at the foot end, the cover comprising a foot end frame and a center spine frame connected to the foot end frame at a first end of the center spine frame, the center spine frame extending over the support bed and spaced from the support bed a desired amount, a second end of the center spine frame terminating short of a head end of the support bed, a hoop frame supported on the second end of the center spine frame and extending outwardly and downwardly to a level of the base unit at opposite sides of the base unit when the cover is in a closed position, and a separate cover panel supported on the foot end frame, the center spine frame and the hoop frame, the separate cover panel extending downwardly from the center spine frame to the side edges of the base unit to enclose the support bed when the cover is in the closed position.

2. The personal therapy compartment of claim 1, wherein the cover panel comprises a roughened surface translucent plastic that is molded as a single panel and extends from one longitudinal side edge of the cover to an opposite side longitudinal edge of the cover and which is supported on the hoop frame at the head end.

3. The personal therapy compartment of claim 2, wherein the foot end frame defines a first compartment region, and the center spine frame has spaced longitudinally extending side members defining a second elongated compartment along the center spine frame on an interior of the cover panel, the first and second compartments joining each other, and lines for functional components in the first and second compartments.

4. The personal therapy compartment of claim 3, wherein the lines comprise water lines and valves in the first compartment for controlling flow from each individual water line from a source to connected lines in the second compartment.

5. The personal therapy compartment of claim 2, wherein said support bed is mounted on a molded support having a rim along opposite sides thereof, and a center portion depressed from the rim, said rim having molded inclined panels facing toward the head end of the bed, the inclined panels being positioned on opposite sides of the molded support and raised from the rim, and multi-colored lights mounted on the inclined panels.

6. The personal therapy compartment of claim 1, further characterized by a plurality of massage shower heads mounted on said support bed and directed upwardly to impinge on a person lying on said support bed.

7. The personal therapy compartment of claim 6, further characterized by a cushion on said support bed, said cushion having openings over the massage shower heads to effectively space a person lying on the cushion from the massage shower heads and permit water to be discharged against a surface of a person lying on the bed.

8. The personal therapy compartment of claim 6, wherein a plurality of said massage shower heads are positioned to align generally with a spine of a person lying on said support bed.

9. The personal therapy compartment of claim 6, wherein said massage shower heads include foot massage shower heads positioned adjacent a foot end of the support bed.

10. The personal therapy compartment of claim 9, wherein said massage shower heads include shower heads that are positioned in the back and shoulder support area of the support bed, and in the foot and leg area of the support bed.

11. The personal therapy compartment of claim 6, further comprising a plurality of infrared heaters in the cover positioned to direct heat toward the support bed.

12. The personal therapy compartment of claim 11, further characterized by a plurality of overhead shower heads mounted on an interior of the cover and over the support bed.

13. The personal therapy compartment of claim 12, further comprising controls for the massage shower heads and the overhead shower heads, and for the infrared heaters, including an interlock circuit to prevent the infrared heaters from being energized when the shower heads are operating.

14. The personal therapy compartment of claim 1, further comprising a mist head on an interior surface of the cover for providing a liquid mist toward the support bed, said mist head being connected to one source of therapy materials from a group consisting of liquid vitamins and liquid hormones.

15. A personal therapy compartment comprising a base unit having a head end, a foot end and spaced side edges, and having a support bed on an interior, a cover hingedly connected to the base unit at the foot end, the cover comprising a frame assembly pivotally connected to the base unit at a first end of the frame assembly, the frame assembly extending over the support bed and spaced from the support bed a desired amount, a second end of the frame assembly terminating short of a head end of the support bed, a separate cover panel supported on the frame assembly to enclose the support bed when the cover is in a closed position, and said cover including a panel portion that extends toward the head end beyond the frame assembly to overlie a head portion of the support bed at the head end of the base unit, and a control panel mounted on the panel portion and hingedly mounted on the cover and operably movable between a position wherein the control panel is accessible to a person lying on the support bed, and a second generally upright position, wherein the control panel is accessible to a person on the exterior of the personal therapy compartment.

16. The personal therapy compartment of claim 15, wherein said control panel comprises an operator control section, and a display panel indicating functions of operation of the personal therapy compartment.

17. A personal therapy compartment comprising a base, a support bed in the base, a cover hingedly connected to the base and movable between an opened and a closed position to form an enclosure for a person on the support bed, a plurality of massage shower heads supported on the support bed and directed upwardly toward the cover in selected regions of the support bed, and a pad on the support bed overlying the support bed, said pad having openings therethrough in alignment with the massage shower heads.

18. The personal therapy compartment of claim 17, wherein said support bed has spaced apart side rims raised above center portions of the support bed which are positioned along longitudinally extended edges of the center portions, the support bed having a head end and a foot end spaced in a longitudinal direction, the shower heads being between the side rims, the rims having longitudinally extending inclined surfaces facing toward the head end, and controllable lights mounted on said inclined surfaces facing toward the head end.

19. The personal therapy compartment of claim 17, wherein said massage shower heads comprise spine massage shower heads aligned in a row in a direction from a head end to a foot end of the support bed along a center portion of the support bed.

20. The personal therapy compartment of claim 19, wherein said massage shower heads further comprise foot massage shower heads adjacent a foot end of the support bed.

21. The personal therapy compartment of claim 17, further comprising a source of water connected to said massage shower heads, and controls to control a spray of water through the massage shower heads upwardly from the support bed.

22. The personal therapy compartment of claim 17, wherein said cover comprises a foot end frame, said foot end frame being hingedly mounted to said base at a foot end of the base, and said cover further comprising a center spine frame connected to the foot end frame to provide structural support for the cover, said center spine frame being spaced above the support bed, and a cover panel that overlies the support bed and extends along longitudinal edges of the base attached to the center spine frame.

23. The personal therapy compartment of claim 22, wherein said cover panel has translucent side panel sections on each side from the center spine member to the longitudinal edges, said side panel sections comprising roughed surface translucent plastic material, said side panel sections joined to a center cover panel section, the cover panel comprising a single molded panel that extends from one longitudinal edge of the base to an opposite longitudinal edge of the base and across the center spine frame when the cover is in a closed position.

* * * * *